US00PP16408P3

(12) United States Plant Patent

Lim et al.

(10) Patent No.: US PP16,408 P3

(45) Date of Patent: Apr. 4, 2006

(54) FLORIBUNDA ROSE PLANT NAMED 'BAIPREZ'

(50) Latin Name: *Rosa hybrida*
Varietal Denomination: BAIprez

(75) Inventors: Peter P. Lim, Yamhill, OR (US); Jerry Twomey, Leucadia, CA (US)

(73) Assignee: CP Delaware, Inc., Wilmington, DE (US)

( * ) Notice: Subject to any disclaimer, the term of this patent is extended or adjusted under 35 U.S.C. 154(b) by 180 days.

(21) Appl. No.: 10/900,135

(22) Filed: Jul. 28, 2004

(65) Prior Publication Data

US 2006/0026723 P1 Feb. 2, 2006

(51) Int. Cl.
*A01H 5/00* (2006.01)

(52) U.S. Cl. ..... Plt./143

(58) Field of Classification Search ..... Plt./143, Plt./141, 130

See application file for complete search history.

(56) References Cited

U.S. PATENT DOCUMENTS

PP11,517 P * 9/2000 Carruth ..... Plt./143

OTHER PUBLICATIONS

Hartmann et al. Plant Propagation Principles and Practices. 1983. Prentice–Hall, Inc., 4 th edition, pp. 200–202.*

* cited by examiner

*Primary Examiner*—Anne Marie Grunberg
*Assistant Examiner*—June Hwu
(74) *Attorney, Agent, or Firm*—Burns, Doane, Swecker & Mathis, LLP

(57) ABSTRACT

A new and distinct variety of rose plant of the Floribunda Class is provided which abundantly forms on a nearly continuous basis attractive semi-double self-cleaning blossoms with reflexed yellow-orange petals that are strongly bordered in red. A very short time between bloom cycles is observed. The growth habit is vigorous, compact, and bushy. Dark green glossy foliage is formed in abundance that contrasts nicely with the blossom coloration. Above average disease resistance, especially with respect to Black Spot is displayed. The blossoms possess a slight spice fragrance, and no hips have formed during observations to date. The new variety is well suited for providing distinctive ornamentation in the garden.

3 Drawing Sheets

Botanical/commercial classification: *Rosa hybrida*/Floribunda Rose Plant.
Varietal denomination: cv. 'BAIprez'.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) of the new variety was the 'Playboy' variety (non-patented in the United States). The male parent (i.e., the pollen parent) was the 'Earth Song' variety (non-patented in the United States). The parentage of the new variety can be summarized as follows:

'Playboy'×'Earth Song'.

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) exhibits a vigorous, compact and bushy growth habit, (b) forms in abundance on a nearly continuous basis attractive semi-double self-cleaning blossoms with reflexed yellow-orange petals that are strongly bordered with red, (c) forms abundant dark green glossy foliage that contrasts nicely with the blossom coloration, and (d) exhibits above average resistance to Black Spot.

The new variety well meets the needs of the horticultural industry. It is particularly well suited for providing distinctive ornamentation in the garden.

The new variety can be readily distinguished from its parental varieties. More specifically, the 'Playboy' variety forms single blossoms that are yellow blushed with orange, bear bright yellow stamens, and readily set hips. The 'Earth Song' variety forms Tyrian Red to Tyrian Rose blossoms that include substantially more petals.

The new variety of the present invention possesses a combination of characteristics that differs from that of the 'Wekplapic' variety (U.S. Plant Pat. No. 11,517) that is marketed under the BETTY BOOP trademark. The petals of the new variety are yellow-orange with a red border while those of the 'Wekplapic' variety are ivory-yellow with a red border. The blossoms of the new variety commonly possess more (e.g., approximately 15 to 18) petals and are more tightly aligned. The blossoms of the 'Wekplapic' variety commonly possess approximately 6 to 12 petals. Also, the new variety readily sets hips at West Grove, Pa., U.S.A., and the 'Wekplapic' variety does not set hips at such location.

The new variety of the present invention also can be readily distinguished from the 'Meimonblan' (U.S. Plant Pat. No. 12,579) and 'Meizebul' (U.S. Plant patent application Ser. No. 10/870,155, filed Jun. 18, 2004) varieties. The blossoms of the 'Meimonblan' variety are completely tangerine orange in color, and possess a lesser number of petals. The 'Meizebul' variety forms slightly fragrant salmoncolored blossoms having more petals. The blossoms of the new variety of the present invention possess no fragrance.

The new variety has been found to undergo asexual propagation at Wasco, Calif., U.S.A., by budding. Such asexual propagation has shown that the characteristics of the new variety are strictly transmissible from one generation to another, and that the new variety can be asexually propagated in a true to type manner.

The new variety has been named the 'BAIprez' variety.

BRIEF DESCRIPTION OF THE PHOTOGRAPHS

The accompanying photographs show as nearly true as it is reasonably possible to make the same in color illustrations of this character typical specimens of the new variety. The rose plants of the new variety were two years of age and were photographed on Jun. 10, 2004 while growing in a garden setting on 'Dr. Huey' rootstock at West Grove, Pa., U.S.A.

DETAILED DESCRIPTION

Figure 1:
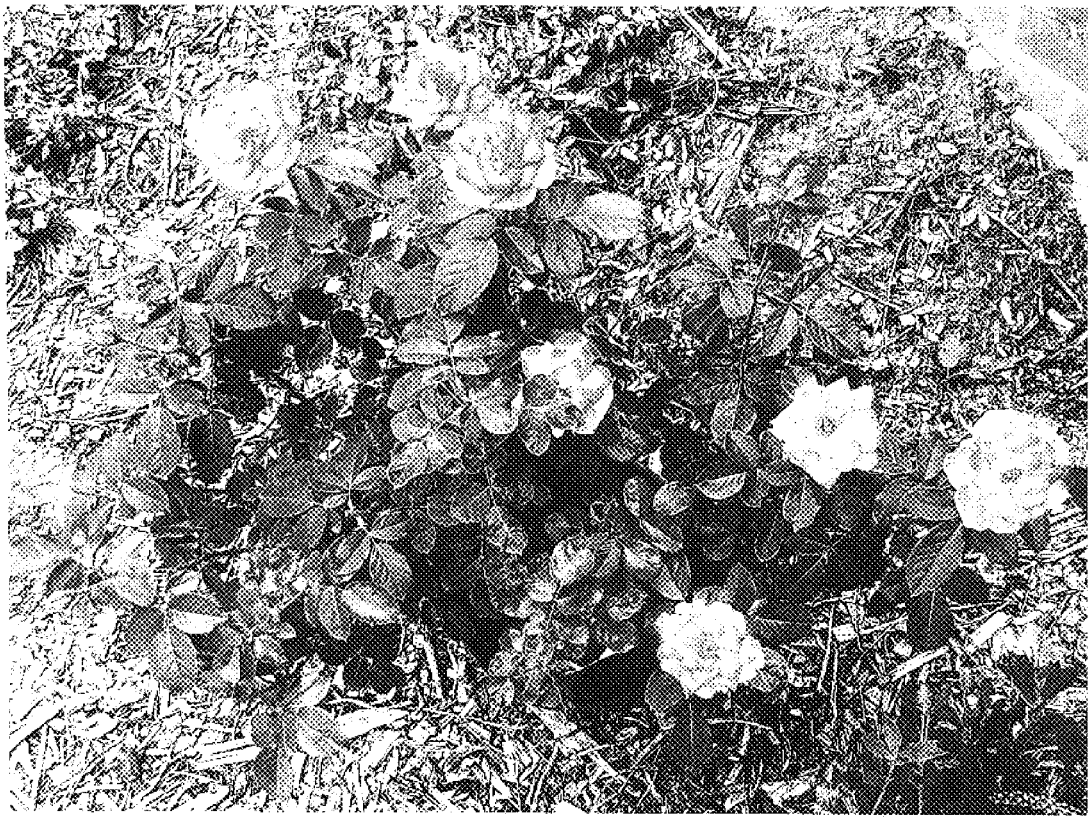
FIG. 1 illustrates from above a flowering plant of the 'BAIprez' variety where the blossoms are at full maturity.
Figure 2:
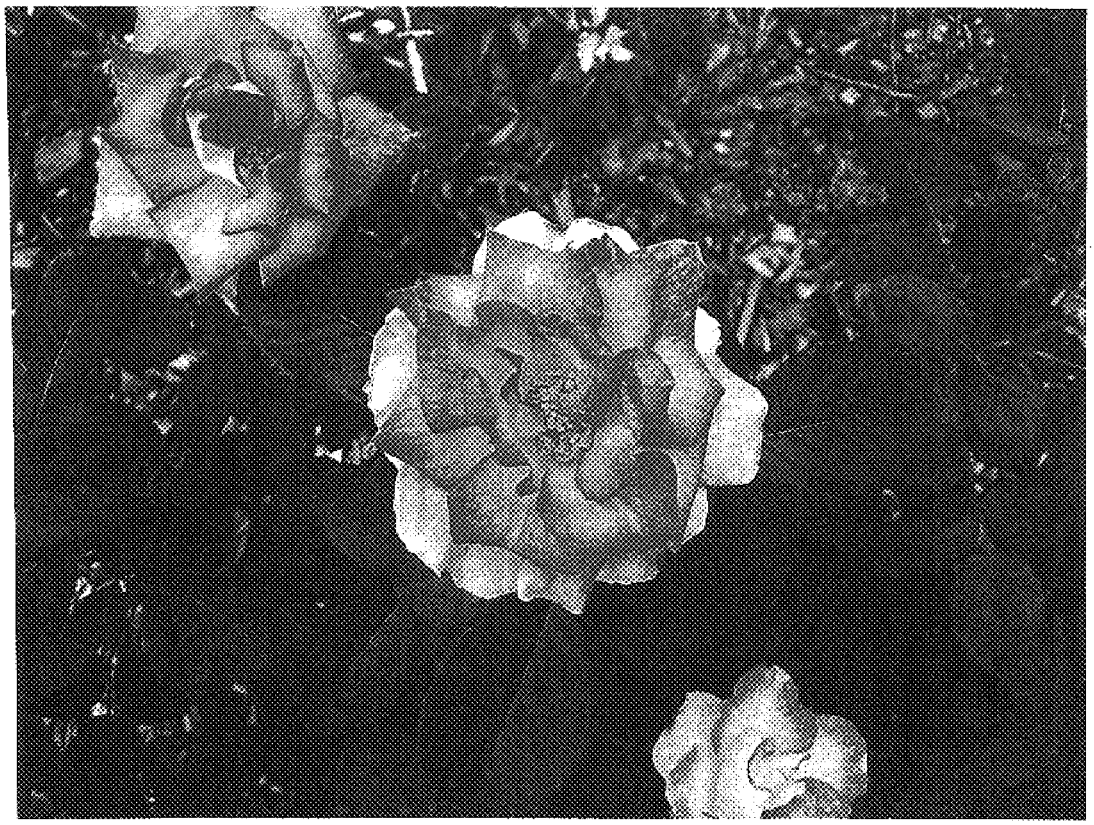
FIG. 2 illustrates three open blossoms at medium maturity and the attractive dark green glossy foliage of the 'BAIprez' variety.
Figure 3:
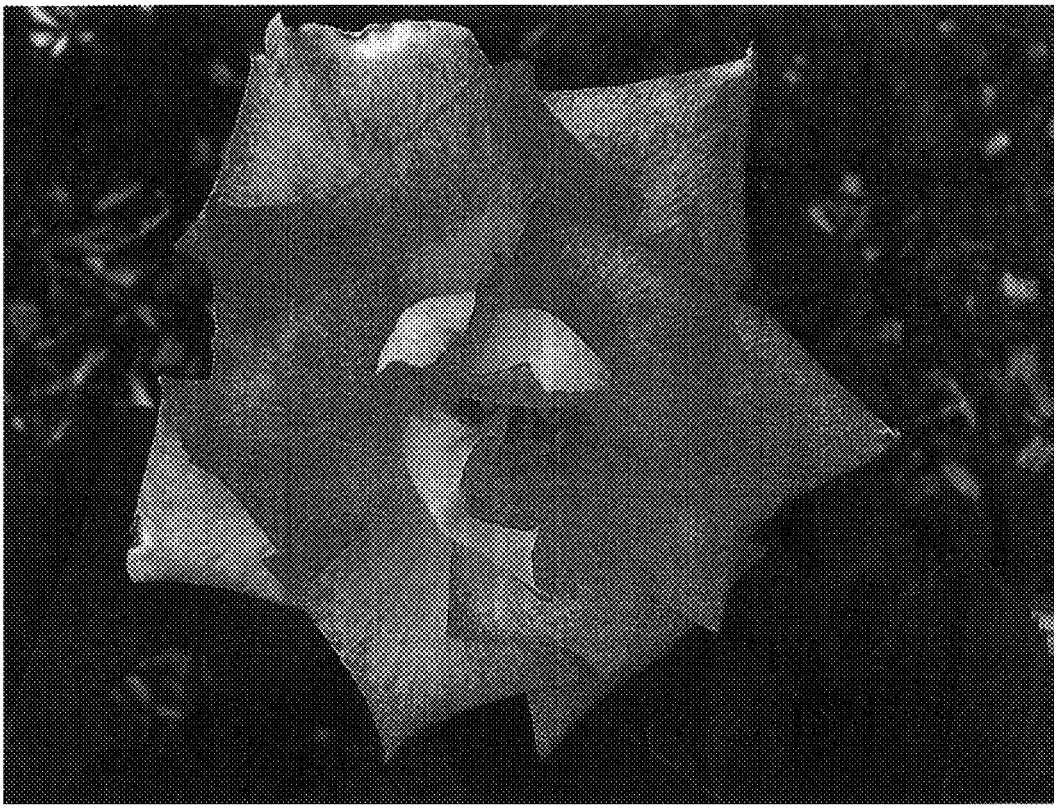
FIG. 3 illustrates a close view from above of a newly-opened blossom of the 'BAIprez' variety.

The chart used in the identification of the colors is that of The Royal Horticultural Society (R.H.S. Colour Chart). The description is based on the observation of two year-old specimens of the new variety which were observed during June 2004 while growing outdoors on 'Dr. Huey' rootstock at West Grove, Pa., U.S.A.

Class: Floribunda.

Plant:

*Height.*—Approximately 90 to 140 cm on average at the end of the growing season.

*Width.*—Approximately 105 to 130 cm on average at the end of the growing season.

*Habit.*—Compact and bushy.

Branches:

*Color.*—Young stems: commonly between Yellow-Green Group 144A and Yellow-Green Group 146B, and often moderately suffused with Greyed-Red Group 178A to Greyed-Purple Group 183D. Adult wood: commonly between Yellow-Green Group 144B and Yellow-Green Group 146C.

*Thorns.*—Some large thorns of approximately 0.8 to 1.3 cm in length, almost straight and angled slightly downwards with a moderately narrow base, and near Yellow-Green Group 144B in coloration, as well as a very few smaller prickles of similar shape and coloration.

Leaves:

*Arrangement.*—Alternate and pinnately compound.

*Size.*—Commonly approximately 8 to 12 cm in length, and approximately 6 to 10 cm in width at the widest point.

*Leaflets.*—Number: commonly 3 or 5 and formed in abundance. Length: approximately 5 to 7 cm. Width: approximately 3 to 5 cm at the widest point. Shape: typically ovate to elliptical. Apex: acute to cuspidate. Base: generally obtuse. Texture: very glossy, and physically moderately thick. Margin: serrate. Venation: pinnate. General appearance: compact, rather dense, dark green, and very glossy. Color (young foliage): Upper surface: commonly between Green Group 137C and Yellow-Green Group 144A, and usually suffused with between Greyed-Purple Group 183A and Greyed-Purple Group 187A. Under surface: commonly between Green Group 138B and Yellow-Green Group 144B, often moderately suffused with Greyed-Purple Group 183B. Color (adult foliage): Upper surface: commonly between Green Group 137A and 139A. Under surface: commonly between Yellow-Green Group 147B and 147C.

*Petiole.*—Length: commonly approximately 24 mm on average. Diameter: commonly approximately 2 mm on average. Surface texture: smooth. Color: commonly between Green Group 137A and Green Group 139A.

*Rachis.*—Somewhat smooth in texture, average caliper, the upper side is moderately grooved with some stipitate glands on the edges of the grooves and sometimes suffused with near Greyed-Purple Group 183B, and the underside is moderately smooth with a few stipitate glands and sometimes with 1 or 2 very small prickles.

*Stipules.*—Size: commonly approximately 0.7 to 1.2 cm in length, and moderately narrow in width with medium long points that often turn out at an angle of more than 45 degrees. Color (adult foliage): Upper surface: commonly between Green Group 137A and Green Group 139A. Under surface: commonly between Yellow-Green Group 147B and 147C.

Inflorescence:

*Number of flowers.*—Singly, and commonly in irregularly rounded clusters of 3 or 4 per stem on strong short to medium length stems of approximately 16 to 22 cm. A very short time between bloom cycles has been observed.

*Peduncle.*—Erect, commonly approximately 2.2 to 4.2 cm in length, average to heavy caliper, moderately smooth, with many stipitate glands and few hairs, between Green Group 137C and Yellow-Green Group 144A, and sometimes moderately blushed on the side exposed to the sun between Greyed-Red Group 178A and Greyed-Purple Group 183B.

*Sepals.*—Number: five. Texture: the inner surfaces are covered with fine wooly tomentum, the margins are lined with many stipitate glands and hairs, and sometimes 1 or 2 or more small slender foliaceous extensions are present. Length: commonly approximately 30 mm on average. Width: commonly approximately 8 mm on average at the widest point. Color: Yellow-Green Group 144C at the base and gradually changing to Yellow-Green Group 144A at the apex with some streaks of Red-Purple Group 59C on the outer surface.

*Buds.*—Shape: commonly very pointed to ovoid with a conspicuous hypanthium. Size: before the calyx breaks commonly approximately 1.2 to 1.6 cm in diameter at the widest point and approximately 1.7 to 2.5 cm in length, and after the calyx breaks approximately 1.7 to 2.2 cm in diameter at the widest point and approximately 2.4 to 2.8 cm in length. Texture: commonly bear a few stipitate glands and hairs. Color: before the calyx breaks between Green Group 137C and Yellow-Green Group 144A, and sometimes moderately blushed on the side exposed to the sun between Greyed-Red Group 178A and Greyed-Purple Group 183B.

*Flower.*—Form: semi-double, and moderately high centered when partially open, and flat to cupped when fully opened. Diameter: commonly approximately 7 to 9 cm when fully open. Color when newly opened: Upper surface: between Yellow Group 13C and Yellow-Orange Group 15D suffusing to a broad edge of between Red Group 46A and Red Group 53B, and near Yellow Group 7A at a small zone at the point of attachment. Under surface: between Yellow Group 13C and Yellow-Orange Group 15D suffusing gradually towards the edge between Red Group 46B and Red Group 53B, and Yellow Group 7C at a small zone at the point of attachment. Color three day-old flower: Upper surface: at the interior portion between Red Group 49D and White Group 155B suffusing to a very broad edge between Red Group 53B and 53C, and Yellow Group 8C at a small zone at the point of attachment. Under surface: at the interior portion between Yellow Group 11D and Yellow-Orange Group 19D suffusing gradually to a moderately thin edge between Red Group 53B and 53C, and Yellow Group 8B at a small zone at the point of attachment. Color of spent bloom: between Red Group 49D and White Group 155B edged with Red Group 53C to 53D. Petal configuration: typically nearly round to broadly obovate with apices that commonly are rounded to sometimes murcronate, moderately indulated, and reflexed. Petal length: commonly approximately 39 mm on average. Petal width: commonly approximately 34.3 mm on average. Petal number: commonly approximately 15 to 20. Petaloids: commonly approximately 1 to 3 arranged irregularly, commonly approximately 11 mm in length on average, commonly approximately 6 mm in width on average, and Red Group 49D blended with White Group 155B in coloration. Petal arrangement: spiraled. Petal texture: physically medium to thick in thickness, very satiny to somewhat velvety on the upper surface, and moderately shiny to satiny on the under surface. Fragrance: slight spiced-tea. Pistils: approximately 70 on average, and approximately 7 mm in length. Stigmas: near Yellow-Orange Group 18A in coloration. Styles: moderately short, somewhat uneven, thin to average in caliper, very bunched, and near Red Group 50A in coloration. Ovaries: typically enclosed in the calyx. Stamen number: commonly approximately 110 on average, and arranged regularly about the pistils. Filaments: commonly approximately 10 mm in length, most bear anthers, and between Yellow-Orange Group 19A and 20A in coloration. Anthers: medium in size, commonly approximately 3.9 mm in length on average, commonly approximately 1.7 mm in width on average, all open at substantially the same time, and between Yellow-Orange Group 19A to 20A in coloration. Pollen: formed in a somewhat sparse quantity and near Yellow-Orange Group 16C in coloration. Lasting quality: approximately 4 or 5 days or more on the plant depending upon the environmental conditions that are encountered. Petal drop: the petals commonly detach cleanly.

Development:

*Vegetation.*—Very vigorous.

*Blooming.*—Abundant and nearly continuous.

*Hardiness.*—Has been shown to grow well in U.S.D.A. Hardiness Zone Nos. 6A to 9A to date. Further cold hardiness testing is underway.

*Aptitude to bear fruit.*—None observed under growing conditions at West Grove, Pa., U.S.A.

*Resistance to diseases.*—Above average disease resistance with respect to Black Spot and Powdery Mildew when compared to other commercial Floribunda varieties at West Grove, Pa., U.S.A.

Plants of the new 'BAIprez' variety have not been observed under all possible environmental conditions to date. Accordingly, it is possible that the phenotypic expression may vary somewhat with changes in light intensity and duration, cultural practices, and other environmental conditions.

I claim:

1. A new and distinct variety of Floribunda rose plant characterized by the following combination of characteristics:

(a) exhibits a vigorous, compact and bushy growth habit, (b) forms in abundance on a nearly continuous basis attractive semi-double self-cleaning blossoms with reflexed yellow-orange petals that are strongly bordered with red, (c) forms abundant dark green glossy foliage that contrasts nicely with the blossom coloration, and (d) exhibits above average resistance to Black Spot, substantially as herein shown and described.

* * * * *